US008524628B2

(12) United States Patent
Jeon et al.

(10) Patent No.: US 8,524,628 B2
(45) Date of Patent: Sep. 3, 2013

(54) PHOSPHORUS-CONTAINING CATALYST COMPOSITION AND HYDROFORMYLATION PROCESS USING THE SAME

(75) Inventors: You Moon Jeon, Daejeon (KR); Dong Hyun Ko, Daejeon (KR); O Hak Kwon, Daejeon (KR); Sung Shik Eom, Daejeon (KR); Sang Gi Lee, Daejeon (KR); Ji Joong Moon, Daejeon (KR); Kwang Ho Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 483 days.

(21) Appl. No.: 10/575,147

(22) PCT Filed: Jul. 3, 2004

(86) PCT No.: PCT/KR2004/001646
§ 371 (c)(1),
(2), (4) Date: Apr. 7, 2006

(87) PCT Pub. No.: WO2005/120705
PCT Pub. Date: Dec. 22, 2005

(65) Prior Publication Data
US 2007/0123735 A1     May 31, 2007

(30) Foreign Application Priority Data
Jun. 12, 2004    (KR) .......................... 10-2004-0043334

(51) Int. Cl.
*B01J 31/22*   (2006.01)
*C07F 9/06*    (2006.01)

(52) U.S. Cl.
USPC .......................................... 502/155; 548/412

(58) Field of Classification Search
USPC .......................................... 502/155; 548/412
See application file for complete search history.

(56) References Cited

U.S. PATENT DOCUMENTS

| | | | |
|---|---|---|---|
| 4,201,714 A | 5/1980 | Hughes | |
| 4,450,299 A | 5/1984 | Oswald et al. | 568/454 |
| 4,482,749 A | 11/1984 | Dennis et al. | |
| 4,496,769 A | 1/1985 | Dennis et al. | |
| 4,668,651 A | 5/1987 | Billig et al. | 502/158 |
| 4,694,109 A | 9/1987 | Devon et al. | 568/454 |
| 5,233,093 A | 8/1993 | Pitchai et al. | 568/454 |
| 5,491,266 A | 2/1996 | Babin et al. | 568/449 |
| 5,567,856 A | 10/1996 | Unruh et al. | |
| 5,710,344 A | 1/1998 | Breikss et al. | 568/451 |
| 5,910,600 A | 6/1999 | Urata et al. | |
| 5,962,744 A | 10/1999 | Ojima et al. | |
| 6,153,800 A * | 11/2000 | Gelling et al. | 568/454 |
| 2003/0055253 A1 | 3/2003 | Ahlers et al. | |

FOREIGN PATENT DOCUMENTS

| | | |
|---|---|---|
| GB | 2056874 A | 3/1981 |
| JP | 10-265426 | 10/1998 |
| JP | 2859955 | 12/1998 |
| JP | 11-506445 | 6/1999 |
| JP | 2002-47294 A | 2/2002 |
| WO | 90/06810 | 6/1990 |
| WO | 96/38456 | 12/1996 |
| WO | 03/018192 A2 | 3/2003 |
| WO | 03/018192 A3 | 3/2003 |

OTHER PUBLICATIONS van der Slot et al. "Rhodium-Catalyzed Hydroformylation and Deuterioformylation with Pyrroyl-Based Phosphorus Amidite Ligands: Influence of Electronic Ligand Properties" Organometallics, 2002, vol. 21, pp. 3873-3883.*
Billig et al "Oxo Process" Kirk-Othmer Encyclopedia of Chemical Technology, 1996, Wiley and Sons, pp. 1-17.*
Moloy, K.G., et al., "N-Pyrrolyl Phosphines: An Unexploited Class of Phosphine Ligands with Exceptional Acceptor Character," J. Am. Chem. Soc., vol. 117, pp. 7696-7710 (1995).
Bizarri, S.N., et al., "CEH Marketing Research Report: Oxo Chemicals," SRI International, vol. 682.7000 A, pp. 1-121 (2002).
Moloy, Kenneth G., et al., "N-Pyrrolyl Phosphines: An Unexploited Class of Phosphine Ligands With Exceptional Acceptor Character," J. Am. Chem. Soc., 1995, 117, 7696-7710.
Bizzari, Sebastian N., et al., "CEH Marketing Report—Oxo Chemicals," Nov. 2002, 682.7000A, 1-121.
European Search Report issued Apr. 6, 2009 for Appln. No. 04774072.5-210411756782, corresponding to PCT Application No. PCT/KR2004001646.
Leeuwen, et al., Phosphines as Ligands, Bite angle effects for diphosphines, Institute of Molecular Chemistry, University of Amsterdam, 2000 Kluwer Academic Publishers, pp. 63-105.
Dieguez, et al., High-Pressure Infrared Studies of Rhodium Complexes Containing Thiolate Bridge Ligands Under Hydroformylation Conditions, Institute of Molecular Chemistry, University of Amsterdam, Organometallics 1999, 18, 2107-2115.
Slot, et al., Rhodium-Catalyzed Hydroformylation and Deuterioformylation With Pyrrolyl-based Phosphorus Amidite Ligands; Influence of Electronic Ligand Properties, Institute of Molecular Chemistry, University of Amsterdam, Organometallics 2002, 21. 3873-3883.
Japanese Non-Final Office Action; Dated Apr. 21, 2009.

(Continued)

*Primary Examiner* — Joseph Kosack
(74) *Attorney, Agent, or Firm* — McKenna Long & Aldridge LLP

(57) ABSTRACT

Provided are a catalyst composition comprising a bidentate ligand, a monodentate ligand, and a transition metal catalyst and a process of hydroformylation of olefin compounds, comprising reacting the olefin compound with a gas mixture of hydrogen and carbon monoxide while being stirred at elevated pressures and temperatures in the presence of the catalyst composition to produce an aldehyde. The catalytic composition demonstrates the high catalytic activity and option control of selectivity to normal aldehyde or iso aldehyde (N/I selectivity) to a desired value.

8 Claims, No Drawings

(56) References Cited

OTHER PUBLICATIONS

Saskia C. van der Slot, et al.,; Rhodium-Catalyzed Hydroformylation and Deuterioformylation with Pyrrolyl-based Phosphorus Amidite Ligands: Influence of Electronic Ligand Properties; Organometallics, vol. 21, No. 19, 2002; pp. 3872-3883.

European Patent Office Communication dated Jul. 16, 2009 for Application. No. 04774072.5-2104.
Official Office Action dated Mar. 1, 2010 by the Japanese Patent Office with English Translation.
E. Billig., "Oxo Process" Kirk-Othmer Encyclopedia of Chemical Technology, 2000, p. 1-17, John Wiley & Sons, Inc.

* cited by examiner

PHOSPHORUS-CONTAINING CATALYST COMPOSITION AND HYDROFORMYLATION PROCESS USING THE SAME

BACKGROUND OF THE INVENTION

1. Field of the Invention

The present invention relates to a phosphorous-containing catalyst composition and a hydroformylation process using the same, and more particularly, to a phosphorous-containing catalyst composition in which a combination of a monodentate phosphorous compound and a bidentate phosphorous compound is used as a ligand to a transition metal catalyst and a process of hydroformylation of olefin compounds comprising reacting the olefin compound with a gas mixture of hydrogen and carbon monoxide while being stirred at elevated pressures and temperatures in the presence of the above catalyst composition to produce aldehyde.

2. Description of the Related Art

The hydroformylation reaction, also known as the oxo reaction, includes reacting an olefin with a synthesis gas ($CO/H_2$) in the presence of a metal catalyst and a ligand to produce a linear (normal) aldehyde and branched (iso) aldehyde which has one more carbon atom than the olefin. The oxo reaction was discovered by Otto Roelen in 1938. In 2001, about 8,400,000 tons of various aldehydes (including its alcohol derivatives) were produced through the oxo reaction worldwide (*SRI Report*, November 2002, 682. 700A). The various aldehydes synthesized according to the oxo reaction are converted to acids and alcohols through oxidation and reduction reactions. The aldehydes may be subjected to an aldol condensation reaction and then converted to acids and alcohols having a long alkyl chain through oxidation and reduction reactions. The obtained acids and alcohols are used as solvents, additives, raw materials for various plasticizers, and etc.

Cobalt (Co) or rhodium (Rh)-based catalysts are mostly used in the oxo reaction. Depending on the types of ligands and the operating conditions, different N/I (ratio of linear (normal) isomer to branched (iso) isomer) selectivity of aldehyde is obtained. At least 70% of all oxo plants have adopted a low pressure oxo process with a rhodium-based catalyst.

In addition to cobalt (Co) and rhodium (Rh), iridium (Ir), ruthenium (Ru), osmium (Os), planitum (Pt), palladium (Pd), iron (Fe), and nickel (Ni) can be used as a central metal in the catalyst for the oxo reaction. Catalytic activities of these metal complexes can be ordered as follows: Rh>>Co>Ir, Ru>Os>Pt>Pd>Fe>Ni. Therefore, most research and development have been focused on rhodium and cobalt. Examples of ligands in the catalyst may include phosphine ($PR_3$, $R=C_6H_5$, $n-C_4H_9$), phosphine oxide ($O=P(C_6H_5)_3$), phosphite, amine, amide, and isonitrile. There rarely exist ligands that are more advantageous in view of catalytic activity, stability, and cost than triphenylphosphine (TPP). Thus, in most oxo reactions, Rh metal is used as a catalyst and TPP and its derivatives are used as ligand. In addition, to increase the stability of a catalytic system, TPP ligand is used in an amount of at least 100 equivalent of the catalyst.

Eastman Kodak Company and Union Carbide Company (merged into Dow) developed a bidentate phosphine ligand having high catalytic activity and high N/I selectivity, respectively (see, U.S. Pat. Nos. 4,694,109 and 4,668,651).

Moloy and coworkers developed N-pyrrolyl phosphine which shows high activity and selectivity (*JACS* 1995, 117, 7696).

U.S. Pat. No. 5,710,344 describes a process for the preparation of linear aldehydes by hydroformylation using a bidentate ligand which contains at least one P—C or P—N bond.

As the application of iso aldehyde is developed, there is an increasing need for iso aldehyde. However, since the conventional catalyst compositions have high selectivity to normal aldehyde, increase of production of iso aldehyde is limited. Thus, there is a need for a process of producing a normal aldehyde and an iso aldehyde in a desired ratio by controlling N/I selectivity while maintaining a sufficient catalytic activity.

SUMMARY OF THE INVENTION

The present invention provides a hydroformylation catalyst composition comprising a bidentate ligand, a monodentate ligand and a transition metal catalyst which can have very high catalytic activity and is able to control N/I selectivity to a desired value.

The present invention also provides a process of hydroformylation of olefin compounds, comprising reacting the olefin compound with a gas mixture of hydrogen and carbon monoxide while being stirred at elevated pressures and temperatures in the presence of the above catalyst composition to produce aldehyde.

According to an aspect of the present invention, there is provided a catalyst composition comprising a bidentate ligand represented by formula 1, a monodentate ligand represented by formula 2, and a transition metal catalyst represented by formula 3:

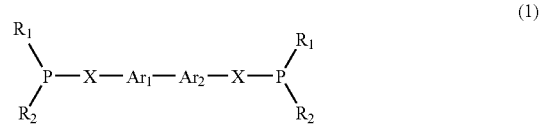

(1)

wherein
each of $R_1$ and $R_2$ is a substituted or unsubstituted C1-20 alkyl group; a substituted or unsubstituted C1-20 alkoxy group; a substituted or unsubstituted C5-20 cycloalkane or cycloalkene; a substituted or unsubstituted C6-36 aryl group; a substituted or unsubstituted C1-20 heteroalkyl group; a substituted or unsubstituted C4-36 heteroaryl group; or a substituted or unsubstituted C4-36 heterocyclic group,
$Ar_1$-$Ar_2$ is a bisaryl compound, and
X is oxygen (O) or sulfur (S),

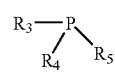

(2)

wherein
each of $R_3$, $R_4$ and $R_5$ is a substituted or unsubstituted C1-20 alkyl group; a substituted or unsubstituted C1-20 alkoxy group; a substituted or unsubstituted C5-20 cycloalkane or cycloalkene; a substituted or unsubstituted C6-36 aryl group; a substituted or unsubstituted C1-20 heteroalkyl group; a substituted or unsubstituted C4-36 heteroaryl group; or a substituted or unsubstituted C4-36 heterocyclic group, each of $R_3$, $R_4$ and $R_5$ being optionally substituted with nitro ($—NO_2$), fluorine (F), chlorine (Cl), bromine (Br), or a $C_{1-4}$ alkyl group, $$M(L_1)_l(L_2)_m(L_3)_n \qquad (3)$$

wherein

M is a transition metal, each of $L_1$, $L_2$ and $L_3$ is hydrogen, CO, acetylacetonato, cyclooctadiene, norbornene, chlorine, or triphenylphosphine, and each of l, m and n is a number of 0 to 5, provided that all l, m and n are not zero, simultaneously.

According to another aspect of the present invention, there is provided a process of hydroformylation of olefin compounds, comprising reacting the olefin compound with a gas mixture of hydrogen and carbon monoxide while being stirred at elevated pressures and temperatures in the presence of the above catalyst composition to produce an aldehyde.

The olefin compound may be represented by formula 4:

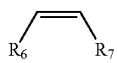

(4)

wherein each of $R_6$ and $R_7$ is hydrogen, a C1-20 alkyl group, fluorine (—F), chlorine (—Cl), bromine (—Br), trifluoromethyl (—CF$_3$), or a C6-20 phenyl group substituted with 0 to 5 substituents selected from the group consisting of nitro (—NO$_2$), fluorine (—F), chlorine (—Cl), bromine (—Br), methyl, ethyl, propyl and butyl.

DETAILED DESCRIPTION OF THE INVENTION

The catalyst composition according to an embodiment of the present invention comprises a bidentate ligand, a monodentate ligand and a transition metal catalyst.

The bidentate ligand represented by formula 1 may be one in which each of $R_1$ and $R_2$ is pyrrole, phenyl, or indole, and the phosphorous is directly linked to a nitrogen atom.

In formula 1, the bisaryl compound $Ar_1$-$Ar_2$ may be represented by either formula 5 or formula 6:

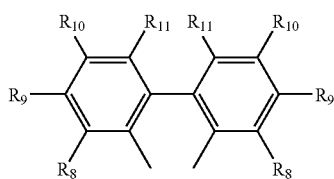

(5)

wherein each of $R_8$, $R_9$, $R_{10}$, and $R_{11}$ is hydrogen, a C1-20 alkyl group, a C6-20 aryl group, a triarylsilyl group, a trialkylsilyl group, a carboalkoxy group, a carboaryloxy group, an aryloxy group, an alkoxy group, an alkylcarbonyl group, an arylcarbonyl group, an amide group, a halogen atom, or a nitrile group, the carboalkoxy group being represented by —CO$_2$R (wherein R is a C1-20 alkyl group or a C6-20 aryl group), and preferably, $R_8$ may be methyl, methoxy, or t-butyl group, $R_9$ may be hydrogen, $R_{10}$ may be methyl, methoxy, or t-butyl, and $R_{11}$ may be methyl or hydrogen,

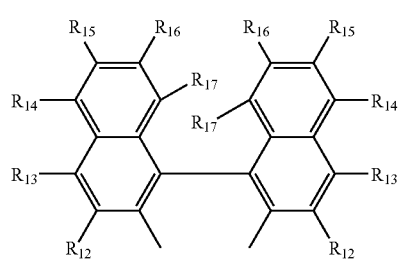

(6)

wherein each of $R_{12}$, $R_{13}$, $R_{14}$, $R_{15}$, $R_{16}$, and $R_{17}$ is hydrogen, a C1-20 alkyl group, a C6-20 aryl group, a triarylsilyl group, a trialkylsilyl group, a carboalkoxy group, a carboaryloxy group, an aryloxy group, an alkoxy group, an alkylcarbonyl group, an arylcarbonyl group, an amide group, a halogen atom, a nitrile group, the carboalkoxy group being represented by —CO$_2$R (wherein R is a C1-20 alkyl group or a C6-20 aryl group).

The monoidentate ligand represented by formula 2 may be one in which each of $R_3$, $R_4$, and $R_5$ is phenyl, phenyloxy, cyclohexyl, or t-butyl.

In the transition metal catalyst, the transition metal M may be cobalt (Co), rhodium (Rh), or iridium (Ir). Specific examples of the transition metal catalyst may include acetylacetonatodicarbonylrhodium (Rh(AcAc)(CO)$_2$), acetylacetonatocarbonyltriphenylphosphinerhodium (Rh(AcAc)(CO)(TPP)), hydridocarbonyltri(triphenylphosphine)rhodium (HRh(CO)(TPP)$_3$), acetylacetonatodicarbonyliridium (Ir(AcAc)(CO)$_2$), or hydridocarbonyltri(triphenylphosphine)iridium (HIr(CO)(TPP)$_3$).

In the catalyst composition, the concentration of the transition metal may be 50 to 500 ppm based on the amount of the catalyst composition. If the concentration of the transition metal is less than 50 ppm, the hydroformylation reaction rate can be reduced, which is not economical. If the concentration of the transition metal is more than 500 ppm, it is disadvantageous in view of costs, since the transition metal is very expensive. In addition, the reaction rate is not advantageously increased, even at a concentration of more than 500 ppm.

The molar ratios of the bidentate ligand and the monodentate ligand to the Rh metal are 0.5 to 20 and 0.1 to 50, respectively. Preferably, the molar ratios of the bidentate ligand and the monodentate ligand to the Rh metal are 1 to 10 and 0.5 to 20, respectively. If the molar ratio of the bidentate ligand to the Rh metal is less than 0.5, the catalytic stability could be reduced. If the molar ratio of the bidentate ligand to the Rh metal is more than 20, the N/I selectivity could be increased, however the catalytic activity could be reduced. If the molar ratio of the monodentate ligand to the Rh metal is less than 0.1, the catalytic activity could be increased, but N/I selectivity cannot be controlled. If the molar ratio of the monodentate ligand to the Rh metal is more than 50 the catalytic stability and the activity could be reduced.

According to the embodiment of the present invention, by varying the molar ratio of the monodentate ligand, the N/I selectivity of the aldehyde produced is optionally controlled while maintaining the same catalytic activity as in the case of using a bidentate ligand alone. It appears that this advantage is derived since the monodentate ligand has a tendency to coordinate to a metal center of the catalyst in competition with the bidentate ligand in a catalytic cycle.

If the molar ratio of the bidentate ligand and the monodentate ligand to the Rh metal are 0.5 to 2 and 1 to 10, respectively, then the N/I selectivity is in a range of 2 to 3. If the molar ratio of the bidentate ligand and the monodentate ligand to the Rh metal are 3 to 10 and 1 to 10, respectively, then the N/I selectivity increase upto 15 to 18.

Advantageously, the transition metal catalyst may be acetylacetonatodicarbonylrhodium ($Rh(AcAc)(CO)_2$), the bidentate ligand may be 1,1'-biphenyl-2,2'-diyl-bis(dipyrrolylphosphoramidite) (BPO—$P(Pyl)_2$), and the monodentate ligand may be triphenylphosphine (TPP).

The olefin compound may be a compound selected from the group consisting of ethene, propene, 1-butene, 1-pentene, 1-hexene, 1-octene, and styrene.

The solvent used in the hydroformylation reaction according to the embodiment of the present invention may include aldehydes, such as propane aldehyde, butyraldehyde, and valeraldehyde; ketones, such as acetone, methyl ethyl ketone, methyl isobutyl ketone, acetophenone, and cyclohexanone; aromatics, such as benzene, toluene, and xylene; halogenated aromatics including ortho-dichlorobenzene; ethers, such as tetrahydrofuran, dimethoxy ethane, and dioxane; halogenated paraffins including methylene chloride; paraffinic hydrocarbons such as heptane, preferably various aldehydes and aromatics, such as toluene.

The composition of the synthesis gas $CO/H_2$ used in the hydroformylation reaction according to the embodiment of the present invention can vary within a wide range. The molar ratio of $CO/H_2$ may be generally about 5:95 to 70:30, preferably about 40:60 to 60:40, and especially preferably about 1:1.

The temperature of the hydroformylation reaction may be generally about 20 to 180° C., preferably about 50 to 150° C. The pressure of the hydroformylation reaction may be generally about 1 to 700 bar, preferably 1 to 300 bar.

Hereinafter, the present invention will be in more detail explained with reference to the following examples and not intended to limit the scope of the present invention.

Examples 1 to 9

Hydroformylation of Propene Using Acetylacetonatodicarbonylrhodium ($Rh(AcAc)(CO)_2$) Catalyst, a Bidentate Phosphorous Compound and a Monodentate Phosphorous Compound 10.0 mg (37.8 mmol) of $Rh(AcAc)(CO)_2$ catalyst, 0.2 mL of hexadecane, which is an internal standard of GC analysis, BPO—$P(Pyl)_2$ as a bidentate ligand and ether TPP (triphenylphosphine) or TPPI (triphenylphosphite) as a monodentate ligand were added in toluene so that a total amount of the solution is 100 mL, each ratio of the bidentate ligand and the monodentate ligand to rhodium being listed in Table 1, and charged into a reactor (High Throughput Screening Unit (HTS), manufactured by Auto Clave). A gas mixture of propene:CO:$H_2$ in a molar ratio of 1:1:1 was injected into the reactor to maintain a pressure at 6 bar. Then, the mixture was reacted while being stirred at 85° C. for 2.5 hours.

The applied catalyst and ligands, the molar ratio of each ligand to the catalyst, the reaction temperature, the N/I selectivity, and the catalytic activity were listed in Table 1.

In Table 1, the N/I value represent the relative ratio of normal-butyraldehyde to iso-butyraldehyde produced. Each yield of the aldehyde was obtained by GC analysis based on the amount of the hexadecane added as an internal standard.

To calculate the catalytic activity of the each reaction, the total amount of the produced normal butyraldehyde and iso butyraldehyde was divided by the molecular weight of butyraldehyde, by the concentration of the catalyst, and by the reaction time. The catalytic activity is expressed in $mol_{(BAL)}/mol_{(Rh)}/h$.

TABLE 1

| | Catalyst | Ligand 1 (L1) | Ligand 2 (L2) | L1/Rh mol/mol | L2/Rh mol/mol | N/I | Catalytic activity ($mol_{(BAL)}/mol_{(Rh)}/h$) |
|---|---|---|---|---|---|---|---|
| Example 1 | $Rh(AcAc)(CO)_2$ | BPO—$P(Pyl)_2$ | TPP | 1 | 1 | 3.2 | 253.6 |
| Example 2 | $Rh(AcAc)(CO)_2$ | BPO—$P(Pyl)_2$ | TPP | 1 | 3 | 2.0 | 192.2 |
| Example 3 | $Rh(AcAc)(CO)_2$ | BPO—$P(Pyl)_2$ | TPP | 1 | 5 | 2.0 | 175.0 |
| Example 4 | $Rh(AcAc)(CO)_2$ | BPO—$P(Pyl)_2$ | TPP | 1 | 10 | 2.2 | 124.4 |
| Example 5 | $Rh(AcAc)(CO)_2$ | BPO—$P(Pyl)_2$ | TPP | 3 | 1 | 15.7 | 204.4 |
| Example 6 | $Rh(AcAc)(CO)_2$ | BPO—$P(Pyl)_2$ | TPP | 3 | 3 | 17.0 | 130.3 |
| Example 7 | $Rh(AcAc)(CO)_2$ | BPO—$P(Pyl)_2$ | TPP | 5 | 1 | 17.2 | 109.6 |
| Example 8 | $Rh(AcAc)(CO)_2$ | BPO—$P(Pyl)_2$ | TPPI | 1 | 5 | 2.2 | 147.7 |
| Example 9 | $Rh(AcAc)(CO)_2$ | BPO—$P(Pyl)_2$ | TPPI | 3 | 1 | 16.2 | 135.9 |

Comparative Example 1

Hydroformylation of Propene Using Acetylacetonatodicarbonylrhodium (Rh(AcAc)(CO)$_2$) Catalyst and Triphenylphosphine (TPP)

The experiment for catalytic activity was performed in the same manner as in Example 1 except that TPP was used alone as a ligand and a molar ratio of ligand to rhodium was 100. The results are shown in Table 2.

Comparative Example 2

Hydroformylation of Propene Using Acetylacetonatodicarbonylrhodium (Rh(AcAc)(CO)$_2$) Catalyst and Tripyrrolylphosphine P(Pyl)$_3$)

The experiment for catalytic activity was performed in the same manner as in Comparative Example 1 except that P(Pyl)$_3$ was used instead of TPP as a ligand, and a molar ratio of ligand to rhodium was 50. The results are shown in Table 2.

Comparative Example 3

Hydroformylation of Propene Using Acetylacetonatodicarbonylrhodium (Rh(AcAc)(CO)$_2$) Catalyst and 1,1'-biphenyl-2,2'-diyl-bis(dipyrrolylphosphoramidite) (BPO-P(Pyl)$_2$)

The experiments for catalytic activity were performed in the same manner as in Comparative Example 1 except that BPO—P(Pyl)$_2$ was used instead of TPP as a ligand, and molar ratio of ligand to rhodium was 1. The results are shown in Table 2.

TABLE 2

| | Catalyst | Ligand (L) | L/Rh (mol/mol) | Temp. (° C.) | N/I | Catalytic activity (mol$_{(BAL)}$/mol$_{(RH)}$/h) |
|---|---|---|---|---|---|---|
| Comparative Example 1 | Rh(AcAc)(CO)$_2$ | TPP | 100 | 85 | 3.9 | 85.4 |
| Comparative Example 2 | Rh(AcAc)(CO)$_2$ | P(Pyl)$_3$ | 50 | 85 | 10.1 | 80.3 |
| Comparative Example 3 | Rh(AcAc)(CO)$_2$ | BPO—P(Pyl)$_2$ | 1 | 85 | 8.7 | 227.3 |

In Comparative Examples 1 and 2, hydroformylation of propene was performed using a monodentate ligand. As described in Table 2, when TPP was used as a ligand (Comparative Example 1), the catalytic activity was 85.4 mol$_{(BAL)}$/mol$_{(Rh)}$/h and N/I selectivity was 3.9. When tripyrrolylphosphine (P(Pyl)$_3$) was used as a ligand (Comparative Example 2), the catalytic activity was somewhat lower, but the selectivity to normal-butyraldehyde (N/I selectivity 10.1) was somewhat higher than when TPP was used. Especially, it is known that if the temperature of a hydroformylation reaction is decreased when P(Pyl)$_3$ is used as a ligand, the catalytic activity is somewhat decreased, but the N/I selectivity is rapidly increased.

Referring to Table 1, in Example 1, TPP as a monodentate ligand was added in a ratio of 1 mol per mol of rhodium to the catalyst system using a bidentate ligand alone in Comparative Example 3. In this case, the catalytic activity was increased by about 12% and the selectivity to normal butyraldehyde to iso butyraldehyde was reduced from 8.7 to 3.2, i.e., the selectivity to iso butyraldehyde was increased by at least two folds. In Example 2, TPP was added in a ratio of 3 mol per mol of rhodium to the catalytic system using a bidentate ligand alone in Comparative Example 3. In this case, the N/I selectivity was 2.0.

When BPO—P(Pyl)$_2$ as a bidentate ligand was used in a ratio of 3 mol per mol of rhodium, high N/I selectivity of at least 15 was attained, while maintaining high catalytic activity, which was 240% higher compared with Comparative Example 1 using Rh/TPP. When BPO—P(Pyl)$_2$ as a bidentate ligand was used in a ratio of 5 mol per mol of rhodium, the N/I selectivity was increased up to 17.2.

Examples 8 and 9 using TPPI as a monodentate ligand in addition to the bidentate ligand had similar tendencies to the above case using TPP.

From the above results, it is confirmed that using a catalyst composition comprising acetylacetonatodicarbonylrhodium (Rh(AcAc)(CO)$_2$) as a catalyst and a combination of 1,1'-biphenyl-2,2'-diyl-bis(dipyrrolylphosphoramidite) (BPO—P(Pyl)$_2$) as a bidentate ligand and either TPP or TPPI as a monodentate ligand, it is possible to control yields of normal butylaldehyde and iso butylaldehyde.

A catalyst composition comprising a transition metal catalyst and a combination of a monodentate phosphorous compound and a bidentate phosphorous compound as a ligand according to the present invention can be used in a process of hydroformylation of olefin compounds to produce an aldehyde. In a process of hydroformylation of olefin compounds using the catalyst composition comprising a monodentate phosphorous ligand and a bidentate phosphorous ligand according to the present invention, the catalytic activity is very high, and N/I selectivity can be controlled to a desired value.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A catalyst composition for hydroformylating an alpha-olefin compound comprising a bidentate ligand represented by formula 1, a monodentate ligand represented by formula 2, and a transition metal catalyst represented by formula 3:

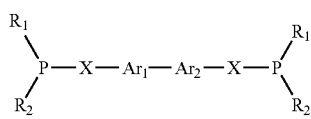

(1)

wherein
each of $R_1$ and $R_2$ is a substituted or unsubstituted C4-36 heteroaryl group,
$Ar_1$-$Ar_2$ is a bisaryl compound, and
X is oxygen (O),
wherein the bisaryl compound $Ar_1$-$Ar_2$ is represented by either formula 5 or formula 6:

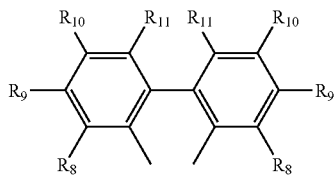
(5)

wherein
each of $R_8$, $R_9$, $R_{10}$, and $R_{11}$ is hydrogen, a C1-20 alkyl group, a C6-20 aryl group, a triarylsilyl group, a trialkylsilyl group, a carboalkoxy group, a carboaryloxy group, an aryloxy group, an alkoxy group, an alkylcarbonyl group, an arylcarbonyl group, an amide group, a halogen atom, or a nitrile group, the carboalkoxy group being represented by —$CO_2R$ (wherein R is a C1-20 alkyl group or a C6-20 aryl group),

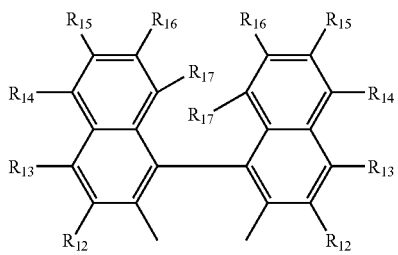
(6)

wherein
each of $R_{12}$, $R_{13}$, $R_{14}$, $R_{15}$, $R_{16}$, and $R_{17}$ is hydrogen, a C1-20 alkyl group, a C6-20 aryl group, a triarylsilyl group, a trialkylsilyl group, a carboalkoxy group, a carboaryloxy group, an aryloxy group, an alkoxy group, an alkylcarbonyl group, an arylcarbonyl group, an amide group, a halogen atom, or a nitrile group, the carboalkoxy group being represented by —$CO_2R$ (wherein R is a C1-20 alkyl group or a C6-20 aryl group),

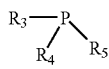
(2)

wherein
each of $R_3$, $R_4$ and $R_5$ is a substituted or unsubstituted C1-20 alkoxy group; a phenoxy group; a substituted or unsubstituted C4-36 heteroaryl group; or a substituted or unsubstituted C4-36 heterocyclic group, each of $R_3$, $R_4$ and $R_5$ being optionally substituted with nitro (—$NO_2$), fluorine (F), chlorine (Cl), bromine (Br), or a C1-4 alkyl group, $$M(L_1)_l(L_2)_m(L_3)_n \quad (3)$$

wherein
M is rhodium,
each of $L_1$, $L_2$ and $L_3$ is hydrogen, CO, acetylacetonato, cyclooctadiene, norbornene, chlorine, or triphenylphosphine, and
each of l, m and n is a number of 0 to 5, provided that all l, m and n are not zero simultaneously; and
wherein the concentration of rhodium is 50 to 500 ppm based on the amount of the catalyst composition, and per mole of the rhodium, the concentration of the monodentate ligand is 0.1 to 10 mol and the concentration of the bidentate ligand is 0.5 to 2 moles to give a N/I selectivity of 2 to 3, or 3 to 10 moles to give a N/I selectivity of 15 to 18.

2. The catalyst composition of claim 1, wherein in formula 1, each of $R_1$ and $R_2$ is pyrrole or indole, and the phosphorous is directly linked to a nitrogen atom.

3. The catalyst composition of 1, wherein in formula 5, $R_8$ is methyl, methoxy, or t-butyl group, $R_9$ is hydrogen, $R_{10}$ is methyl, methoxy, or t-butyl, and $R_{11}$ is methyl or hydrogen.

4. The catalyst composition of claim 1, wherein the transition metal catalyst is acetylacetonatodicarbonylrhodium (Rh)(CO)$_2$), acetylacetonatocarbonyltriphenylphosphinerhodium (Rh)(CO)(TPP)), hydridocarbonyltri(triphenylphosphine)rhodium (HRh(CO)(TPP)$_3$).

5. The catalyst composition of claim 1, wherein the transition metal catalyst is acetylacetonatodicarbonylrhodium (Rh(AcAc)(CO)$_2$), the bidentate ligand is 1,1'-biphenyl-2,2'-diyl-bis(dipyrrolylphosphoramidite) (BPO—P(Pyl)$_2$), and the monodentate ligand is triphenylphosphite (TPPI).

6. A process of hydroformylating an olefin compound, comprising reacting the olefin compound with a gas mixture of hydrogen and carbon monoxide while being stirred at elevated pressures and temperatures in the presence of the catalyst composition of claim 1 to produce an aldehyde.

7. The process of claim 6, wherein the olefin compound is represented by formula 4:

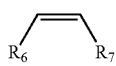
(4)

wherein
each of $R_6$ and $R_7$ is hydrogen, a C1-20 alkyl group, fluorine (—F), chlorine (—Cl), bromine (—Br), trifluoromethyl (—$CF_3$), or a C6-20 phenyl group substituted with 0 to 5 substituents selected from the group consisting of nitro (—$NO_2$), fluorine (—F), chlorine (—Cl), bromine (—Br), methyl, ethyl, propyl and butyl.

8. The process of claim 6, wherein the olefin compound is a compound selected from the group consisting of ethene, propene, 1-butene, 1-pentene, 1-hexene, 1-octene, and styrene.

* * * * *